(12) United States Patent  (10) Patent No.: US 7,706,419 B2
Wang et al.  (45) Date of Patent: Apr. 27, 2010

(54) OPTICAL SYSTEMS FOR MICROARRAY SCANNING

(75) Inventors: Xianhua Wang, Beijing (CN); Guoliang Huang, Beijing (CN); Jing Cheng, Beijing (CN); Hong Zhang, Beijing (CN); Taishan Gao, Beijing (CN)

(73) Assignee: Capitalbio Corporation, Beijing (CN)

( * ) Notice: Subject to any disclaimer, the term of this patent is extended or adjusted under 35 U.S.C. 154(b) by 191 days.

(21) Appl. No.: 11/795,653

(22) PCT Filed: Jun. 3, 2005

(86) PCT No.: PCT/CN2005/000779

§ 371 (c)(1),
(2), (4) Date: Apr. 10, 2008

(87) PCT Pub. No.: WO2006/128325

PCT Pub. Date: Dec. 7, 2006

(65) Prior Publication Data

US 2009/0046756 A1  Feb. 19, 2009

(51) Int. Cl.
H01S 3/10 (2006.01)
(52) U.S. Cl. .................................. 372/24; 382/128
(58) Field of Classification Search ............ 372/66, 372/70, 95, 107, 19, 99
See application file for complete search history.

(56) References Cited

U.S. PATENT DOCUMENTS 4,557,154 A  12/1985  Iwata et al.
6,181,363 B1 *  1/2001  Satoh .................... 347/238
6,355,934 B1 *  3/2002  Osgood et al. .......... 250/458.1
6,471,916 B1  10/2002  Noblett
6,740,871 B1  5/2004  Staton et al.
2002/0062202 A1  5/2002  Arai
2003/0030850 A1  2/2003  Heffelfinger et al.
2003/0161514 A1 *  8/2003  Curry ..................... 382/128
2003/0164814 A1  9/2003  Starkweather et al.
2004/0042007 A1  3/2004  Osipchuk et al.

FOREIGN PATENT DOCUMENTS

CN  2290063 Y  9/1998
CN  1387824 A  1/2003
CN  1534288 A  10/2004

(Continued)

OTHER PUBLICATIONS

U.S. Appl. No. 11/795,652, filed Jun. 2, 2005 by Wang et al.

(Continued)

*Primary Examiner*—Minsun Harvey
*Assistant Examiner*—Tuan N. Nguyen
(74) *Attorney, Agent, or Firm*—Morrison & Foerster LLP

(57) ABSTRACT

The invention provides a novel optical system for use in a microarray scanner, comprising an aperture-containing reflecting mirror comprising an aperture and a reflecting surface. The aperture of the aperture-containing reflecting mirror allows an excitation light to pass through, and the reflecting surface of the aperture-containing reflecting mirror allows emission light from a microarray to be reflected. The optical system may also comprises various other components such as laser generators, beam splitter, reflecting mirrors, excitation and emission light filters, excitation and emission objective lens, pinhole, and detector. The optical system described herein has high efficiency, high sensitivity, low background noise, structurally simple, and high versatility.

13 Claims, 2 Drawing Sheets

FOREIGN PATENT DOCUMENTS

| | | |
|---|---|---|
| JP | 11014609 A | 1/1999 |
| JP | 2002-098639 A | 4/2002 |
| JP | 2003-015442 A | 1/2003 |
| WO | WO 2006/128321 A1 | 12/2006 |
| WO | WO 2006/128322 A1 | 12/2006 |

OTHER PUBLICATIONS

U.S. Appl. No. 11/795,660, filed Jun. 2, 2005 by Wang et al.

* cited by examiner

US 7,706,419 B2

OPTICAL SYSTEMS FOR MICROARRAY SCANNING

TECHNICAL FIELD

This application is in the field of optical systems used in microarray scanning.

BACKGROUND OF THE INVENTION

Developments in microarray-based detection devices have dramatically changed the biotechnology industry. The devices make it possible to analyze multiple biological samples simultaneously and detect rare transcripts in human. They also make it possible to obtain information from microarrays automatically within minutes instead of within months or even years without the help of the devices.

Microarrays typically comprise a plurality of polymers, such as oligonucleotides, peptides, and antibodies. The polymers are synthesized or deposited on a substrate in an array pattern, which can be labeled with optically detectable labels such as fluorescent tags or fluorophores. A typical microarray scanner uses laser as excitation light source, and use matching filters and photomultiplier tubes for detection. During scanning of a microarray, excitation light from the laser source hits different spots on the microarray. Fluorescent probes on the array emit Stokes-shifted light in response to the excitation light, and the emission light is collected by the photomultiplier tube. The resulting information on the microarray can be used for various purposes such as gene expression studies, mutational studies, genotyping, SNP studies, protein interaction analysis, as well as diagnosis and treatment of diseases.

The optical systems used in traditional microarray scanners use beam splitters to separate light beams. As shown in FIG. 1, laser light passes through laser light filter and projects on the beam splitter. Light reflected by the beam splitter then passes through the excitation objective lens, which focuses the light on the surface of the microarray chip. Fluorescent molecules on the microarray that are excited by the laser light emit fluorescent light, which is then collimated by the excitation objective lens and transmits through the beam splitter. Light transmitted through the beam splitter then passes the excitation light filter and become collected by the detector.

There are several drawbacks associated with traditional optical systems. First, incoming laser light loses energy by passing through the beam splitter. Accordingly, the intensity of the excitation light decreases, which in turn decreases the sensitivity of the system. Second, the glass surface of a traditional microarray chip usually reflects 1% or more of the incoming excitation light, which also enters the detection light path. Because in most microarray detection experiments the intensity of the emission light is millions of times weaker than the light intensity of the excitation laser light, light reflected from the glass slide poses significant background problems. Finally, because beam splitters are typically designed for a specific wavelength, they need to be adjusted whenever a new excitation light source is used or when multiple excitation light sources are used. This makes the design of the optical system difficult.

BRIEF SUMMARY OF THE INVENTION

The present invention provides an optical system for microarray laser scanning comprising an aperture-containing reflecting mirror comprising an aperture and a reflecting surface, wherein the aperture on the aperture-containing reflecting mirror allows an excitation light to pass through and wherein the reflecting surface of the aperture-containing reflecting mirror allows emission light from a microarray to be reflected. In some embodiments, the optical system further comprises an excitation objective lens for focusing the excitation light passing through the aperture of the aperture-containing reflecting mirror and/or collimating the emission light from the microarray.

The shape of the aperture of the aperture-containing reflecting mirror described herein can be of any shape, such as a shape selected from the group consisting of circle, oval, regular shape, or irregular shape. The dimension of the aperture can be within any practical range that allows the passage of the excitation light without blockage. For example, when the aperture is a circle, its diameter can (but not necessarily) between about 0.5 mm to about 5 mm, such as between about 0.8 mm to about 0.4 mm, such as between about 1 mm and about 3 mm, such as about 3 mm.

The shape of the aperture-containing reflecting mirror described herein can be of any shape, such as a shape selected from the group consisting of circle, oval, regular shape, or irregular shape. The reflecting mirror can be tilted at any angle relative to the surface of the microarray to be scanned, such as 15°, 20°, 30°, 40°, 45°, 50°, or 60° relative to the surface of the microarray to be scanned.

The optical system may further comprise a light forwarding system for generating the excitation light. In some embodiments, the light forwarding system comprises a laser generator, an optional matching light filter, and an optional first reflecting mirror. In some embodiments, the light forwarding system comprises a first laser generator (with an optional matching light filter), a second laser generator (with an optional light filter), a beam splitter, and a light chopper, wherein the beam splitter transmits laser light generated by the first laser generator and reflects laser light generated by the second laser generator, and wherein the light chopper allows light generated by one laser generator to go through while blocking light generated by another laser generator at each time. In some embodiments, the optical system further comprises a first reflecting mirror optically positioned between the first laser generator and the beam splitter and a second reflecting mirror optically positioned between the beam splitter and the aperture-containing reflecting mirror, wherein light generated by the first laser generator is first reflected by the first reflecting mirror before it is transmitted by the beam splitter, and wherein light coming from the beam splitter is first reflected by the second reflecting mirror before it passes through the aperture of the aperture-containing reflecting mirror. In some embodiments, the light forwarding system further comprises an attenuator optically positioned behind the beam splitter, wherein light coming from the beam splitter is adjusted by the attenuator.

The optical system described herein may further comprise a light collection system for collecting the emission light, comprising a detector (such as a photomultiplier tube) and an emission objective lens optically positioned between the detector and the aperture-containing reflecting mirror. In some embodiments, the light collection system further comprises a pinhole optically positioned between the emission objective lens and the detector.

In some embodiments, the light collection system further comprises an emission light filter optically positioned between the aperture-containing reflecting mirror and the emission objective lens. The emission light filter may comprise a single light filter or multiple light filters (such as 2, 3, 4, 5, 6, 7, 8, 9, or 10 filters) for filtering light of different wavelengths.

In one embodiment, the optical system comprises an aperture-containing reflecting mirror comprising an aperture and a reflecting surface; an excitation objective lens; a light forwarding system comprising a first laser generator; a first reflecting mirror that reflects light generated by the first laser generator, a second laser generator, a beam splitter that transmits light reflected by the first reflecting mirror and reflects light generated by the second laser generator, a light chopper that allows light generated by one laser generator to go through while blocking light generated by another laser generator at a given time, and a second reflecting mirror that reflects the light allowed to go through, wherein light reflected by the second reflecting mirror passes through the aperture of the aperture-containing reflecting mirror and is focused by the objective lens; and a light collection system comprising an emission filter optically positioned behind the aperture-containing reflecting mirror, an emission objective lens optically positioned behind the emission filter, a pinhole optically positioned behind the emission objective lens, and a detector, wherein emission light reflected by the aperture-containing reflecting mirror passes the emission filter, emission objective lens, and pinhole sequentially before it reaches the detector. In some embodiments, the optical system further comprises matching light filter optically positioned in front of at least one of the two laser generators. In some embodiments, the optical system further comprises an attenuator optically positioned between the beam splitter and the second reflecting mirror.

DETAILED DESCRIPTION OF THE INVENTION

Figure 1:
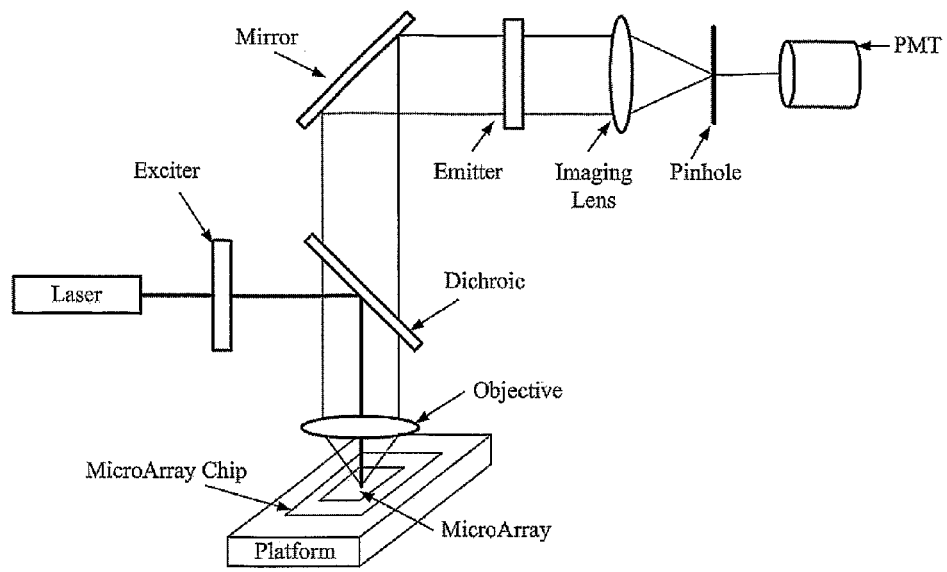
FIG. 1 is a schematic diagram of an optical system for microarray scanning used in prior art.

The present invention provides a novel optical system for microarray analysis that provides high sensitivity, low background noise, and relative simple structure. The optical system comprises an aperture-containing reflecting mirror, which comprises an aperture that allows an excitation light to directly pass through and a reflecting surface that allows emission light from a microarray to be reflected. In some embodiments, the optical system may further comprise an excitation objective lens for focusing the excitation light passing through the aperture of the aperture-containing reflecting mirror and/or collimating emission light from the microarray. In some embodiments, the excitation objective lens is connected to a motor (such as a stepper motor), which moves the objective lens in a direction perpendicular to the surface of the microarray. The position of the objective lens can thus be adjusted in order to focus the excitation light.

Use of the aperture-containing reflecting mirror of the present invention greatly increases the efficiency of the optical system, reduces background noise, and eliminates mutual interference between the excitation light and the emission light. During scanning of a microarray, the excitation light passes through the aperture of the aperture-containing reflecting mirror and becomes directly focused on the microarray to be scanned. Fluorescent light emitted from fluorophores on the microarray is then reflected by the reflecting surface of the aperture-containing reflecting mirror and becomes collected. The excitation light passes the aperture of the aperture-containing reflecting mirror without encountering any blockage, thus reduces light loss. Furthermore, most of the background light reflected from the microarray chip is transmitted through the aperture and does not enter the light collection system. Accordingly, signal-to-noise ratio can be improved.

The aperture of the aperture-containing reflecting mirror can be of any shape, including, but not limited to, circle, oval, square, rectangle, triangle, or other regular or irregular shapes. The dimension of the aperture can be within any practical range that allows the passage of the excitation light without blockage. For example, when the aperture is a circle, its diameter can (but not necessarily) be between about 0.5 mm to about 5 mm, such as between about 0.8 mm to about 0.4 mm, such as between about 1 mm and about 3 mm, such as about 3 mm.

The aperture-containing reflecting mirror can be of any shape, including, but not limited to, circle, oval, square, rectangle, triangle, or other regular or irregular shapes. The reflecting mirror can be tilted at any angle relative to the surface of the microarray to be scanned, such as about any of 15°, 20°, 30°, 40°, 45°, 50°, or 60° relative to the surface of the microarray to be scanned.

In some embodiments, the optical system further comprises a light forwarding system or generating the excitation light. In some embodiments, the light forwarding system of the optical system comprises a laser generator and optionally a reflecting mirror. Light generated from the laser generator is optionally reflected by the reflecting mirror, and the light (reflected or not reflected) passes directly through the aperture of the aperture-containing reflecting mirror. The light forwarding system may further comprise a matching light filter optically positioned in front of the first laser generator, which is used to filter the light generated by the laser generator into narrow-band excitation light.

In some embodiments, the light forwarding system of the optical system comprises a first laser generator (with an optional matching light filter), a second laser generator (with an optional matching filter), a beam splitter, and a light chopper. The two laser generators typically generate light of different wavelengths. The beam splitter is optically positioned so that light generated by the first laser generator is transmitted and light generated by the second laser generator is reflected. The light chopper is optically positioned next to the beam splitter. It allows light generated by one laser generator to go through while blocking light generated by another laser generator at any given time, thus ensures that only one kind of light enters the excitation light path. Use of the light chopper avoids traditional use of rotating reflecting mirrors for selecting laser sources, and thus ensures stability of the optical system.

The optical system (such as the light forwarding system of the optical system) may further comprise one or more reflecting mirrors. The reflecting mirrors are used to alter the direction of the light path, and can be used in any desired manner. For example, there may be a first reflecting mirror optically positioned between the first laser generator and the beam splitter. Light generated by the first laser generator is first reflected by the first reflecting mirror before encountering the beam splitter. In some embodiments, there may be a second reflecting mirror (preferably a proportional reflecting mirror) optically positioned between the beam splitter and the aperture-containing reflecting mirror. Light coming from the beam splitter/light chopper can first be reflected by the second reflecting mirror before it passes directly through the aperture of the aperture-containing reflecting mirror. There can also be a light intensity detector optically positioned to detect light transmitted by the second reflecting mirror. Light signals detected by the light intensity detector can be further converted into digital signals, which can be used to indicate the intensity of the excitation light.

The light forwarding system of the optical system may further comprise an attenuator for controlling and adjusting light intensity of the excitation light. The attenuator may be optically positioned immediately behind the beam splitter so that light combing from the aperture-containing reflecting mirror is adjusted by the attenuator.

As in known in the art, when excitation light scans the microarray, fluorophores on the microarray produce Stoke-shifted emission light in response to the excitation light, which can be collected by a light collection system. Accordingly, in some embodiments, the optical system further comprises a light collection system for collecting emission light from the microarray. The light collection system of the optical system may comprise a detector and an emission objective lens optically positioned between the detector and the aperture-containing reflecting mirror. In some embodiments, the detector is a photomultiplier tube (PMT). The PMT converts incident photons into electrons via the photoelectric effect. A photon strikes the active surface of the PMT (the photocathode), generating an electron. The electron flows through a series of dynodes that multiply the electrons until they reach the anode. The resulting current from the anode is directly proportional to the incident light at the photocathode. The electrical signal can be further amplified by an amplifying filter and converted into digital signals for computer analysis.

In some embodiments, the light collection system of the optical system further comprises a pinhole optically positioned between the emission objective lens and the detector. The pinhole is placed in front of the detector, such that fluorescent light from the microarray that is not within the focal plane where the laser beam was focused (i.e., out-of-focus light) is largely obstructed by the pinhole. In this way, out-of-focus information is greatly reduced.

In some embodiments, the light collection system of the optical system further comprises an emission light filter optically positioned between the aperture-containing reflecting mirror and the emission objective lens. The emission light filter allows light of a desired wavelength to pass through and detected. In some embodiments, the emission light filter comprises two or more (such as 2, 3, 4, 5, 6, 7, 8, 9, 10, or more) light filters for filtering light of different wavelengths (i.e., each allowing light of a different wavelength to pass through). These multiple filters can be arranged in any practical ways. For example, the multiple filters in the emission light filter can be in a circular arrangement (such as in a wheel), and the desired filter is chosen by rotating the emission light filter (i.e., the wheel) so that the desired light filter is optically positioned in the light path.

The choice of the emission light filter(s) depends on the wavelength of the excitation light and the excitation/emission light spectrum of the fluorophores to be detected. The combination of the two laser generators with different matching emission light filters thus allows detection of multiple fluorophores in a sample, either sequentially or simultaneously. Therefore, multiple labels of a sample can be detected using the optical system of the present invention. This is particularly useful in microarray scanning, where multiple probes labeled with different markers are typically used and need to be detected.

In another aspect, the invention provides an optical system comprising (such as consisting of or consisting essentially of) a first laser generator, an aperture-containing reflecting mirror, an excitation objective lens, an emission objective lens, a pinhole, and a detector, wherein the components of the optical system are optically connected. Specifically, light generated by the laser generator passes through the aperture of the aperture-containing mirror, and is focused on the microarray to be scanned by the excitation objective lens. Upon excitation, fluorophores on the microarray to be scanned emit fluorescent light. The emitted light is then collimated by the excitation objective lens and reflected by the aperture-containing reflecting mirror. The reflected emission light passes through the emission objective lens and then the pinhole and is collected by the detector.

In some embodiments, the optical system further includes a second laser generator, a beam splitter and a light chopper. Light generated by the first laser generator is transmitted by the beam splitter, while light generated by the second laser generator is reflected by the beam splitter. The light chopper allows light generated by one laser generator to go through while blocking light generated by another generator at a given time.

In some embodiments, the optical system further includes a first reflecting mirror optically positioned between the first laser generator and the beam splitter. Light generated by the first laser generator is first reflected by the first reflecting mirror before encountering the beam splitter. In some embodiments, there may be a second reflecting mirror (preferably a proportional reflecting mirror) optically positioned between the beam splitter and the aperture-containing reflecting mirror. Light coming from the beam splitter/light chopper can first be reflected by the second reflecting mirror before it passes directly through the aperture of the aperture-containing reflecting mirror. In some embodiments, the optical system may also comprise a light intensity detector that detects light transmitted by the second reflecting mirror.

In some embodiments, the optical system further includes an attenuator optically positioned between the beam splitter and the second reflecting mirror. In some embodiments, the optical system further includes matching light filter placed immediately in front of at least one of the laser generators. In some embodiments, the optical system further includes an emission light filter (such as two or more light filters for filtering light of different wavelength in a complex emission filter) optically positioned between the aperture-containing reflecting mirror and the emission objective lens.

In another aspect, the optical system comprises (such as consists of or consisting essentially of) a first laser generator, a first excitation light filter, a first reflecting mirror, a second laser generator, a second excitation light filter, a beam splitter, a light chopper, a second reflecting mirror, an aperture-containing reflecting mirror, an excitation objective lens, an emission light filter, an emission objective lens, a pinhole, and a detector, wherein the components of the optical system are optically connected.

In some embodiment, the optical system comprises (such as consists of or consists essentially of) a first laser generator, a first excitation light filter, a first reflecting mirror, a second laser generator, a second excitation light filter, a beam splitter, a light chopper, a second reflecting mirror, an aperture-containing reflecting mirror, an excitation objective lens, an emission light filter, an emission objective lens, a pinhole, and a detector, wherein light generated by the first laser generator is filtered by the first excitation light filter, reflected by the first reflecting mirror and transmitted by the beam splitter; wherein laser generated by the second laser generator is filtered by the second excitation light filter and reflected by the beam splitter; wherein the light chopper allows light generated by one laser generator to go through while blocking laser generated by another laser generator at a given time; wherein the light allowed to pass through is reflected by the second reflecting mirror, passes through the aperture of the aperture-containing mirror and is focused on the microarray by the excitation objective lens; wherein emission light from the microarray is collimated by the excitation objective lens, and reflected by the aperture-containing mirror; and wherein the reflected emission light is filtered by the emission light filter, becomes focused by the emission objective lens, passes the pinhole and gets detected by the detector.

The optical system described herein is particularly useful in microarray analysis. "Microarrays" used herein refers to arrays of any biomolecules, including, but not limited to, DNA, RNA, cDNA, polynucleotides, oligonucleotides, proteins, peptides, and antibodies. Microarrays typically comprise a plurality of polymers, e.g., oligomers, synthesized or deposited on a substrate in an array pattern, which are labeled with optically detectable labels such as fluorescent tags or fluorophores. The optical system described herein can be used in scanning microarrays for any use, including, but not limited to, gene expression studies, mutational studies, genotyping, SNP studies, protein interaction analysis, as well as diagnosis and treatment of diseases.

Although the invention is described mostly in the context of microarray scanning, those of skill in the art will understand that it is useful in other applications, such as spectrometry and cytometry applications.

Figure 2:
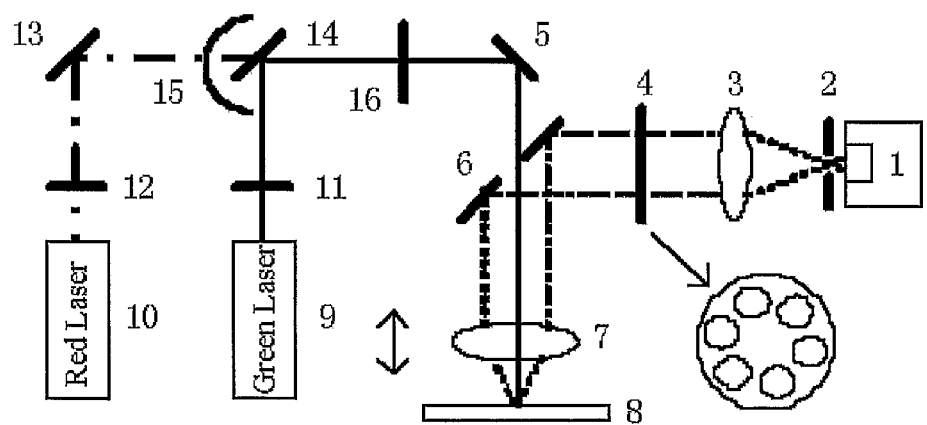
FIG. 2 is a schematic diagram of an exemplary optical system for microarray scanning of the present invention.

FIG. 2 shows one embodiment of the optical system of the present invention. In this embodiment, first laser generator 10 and second laser generator 9 are used to generate laser light of different wavelengths (532 nm and 635 nm, respectively). Excitation light filters 12 and 11 are placed in front of laser generators 10 and 9 respectively to filter the laser light into narrow-band excitation light. Light generated by first laser generator 10 passes through excitation light filter 12, become reflected by first reflecting mirror 13, and is transmitted though beam splitter 14. Light generated by second laser generator 9 passes excitation light filter 11, and is reflected by beam splitter 14. Light chopper 15 is used to make sure that each time only one laser beam passes through. Attenuator 16 is placed between beam splitter 14 and second reflecting mirror 5 to control the intensity of the excitation light. The excitation light is reflected by second reflecting mirror 5. The reflected light directly passes the aperture of aperture-containing reflecting mirror 6 and projects on excitation objective lens 7, which focuses the light on the surface of microarray chip 8. Upon excitation, fluorophores on the microarray chip emits fluorescent emission light.

The emission light coming from the microarray chip becomes collimated by excitation objective lens 7, and the collimated light is reflected by the reflecting surface of aperture-containing reflecting mirror 6. The reflected emission light passes through one of the light filters of complex emission light filter 4, which contains 6 different light filters. The filtered light becomes focused by emission objective lens 3. Pinhole 2 blocks background signals, allowing only focused light to come through. Light passing the pinhole is then collected by PMT 1.

Figure 3:
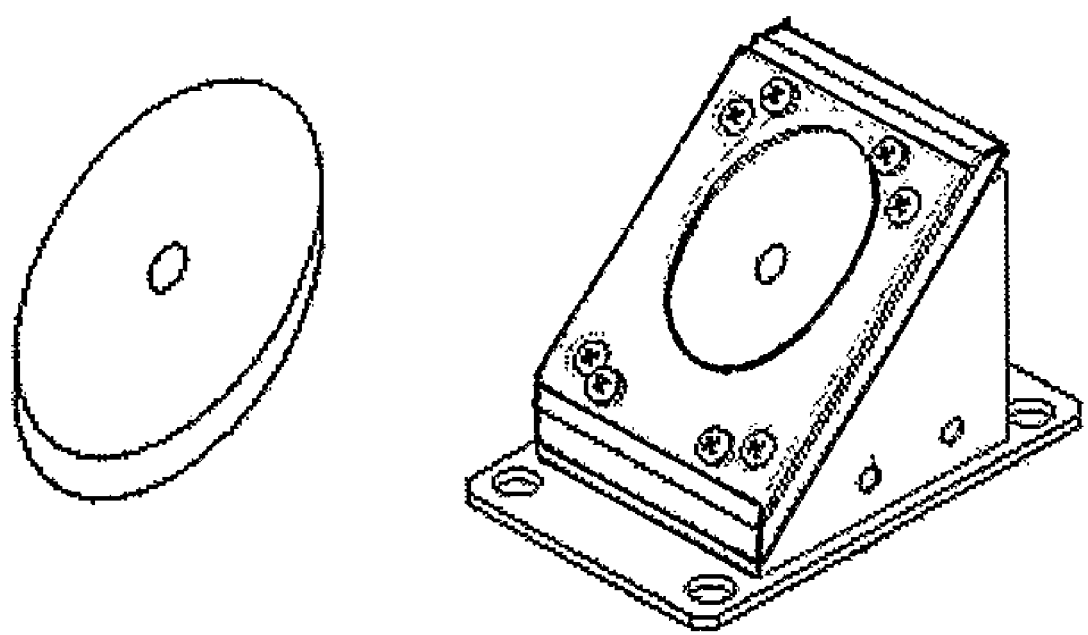
FIG. 3 is a schematic diagram of an exemplary aperture-containing reflecting mirror used in the present invention.

FIG. 3 shows one embodiment of the aperture-containing reflecting mirror used in the optical system of the present invention. The mirror has an oval shape and is tiled 45° relative to the horizontal surface. A circular aperture with a 3 mm diameter is present at the center of the mirror, which allows excitation light to pass through without blockage. One side of the mirror has a reflecting surface for reflecting the emission light. In this arrangement, the excitation light path is perpendicular to the collection light path, and does not interfere with each other.

Although the foregoing invention has been described in some detail by way of illustration and example for purpose of clarity and understanding, it will be apparent to those of skill in the art that certain changes and modifications can be practiced. Therefore, the description and examples should not be construed as limiting the scope of the invention, which is delineated by the appended claims. All the drawings, the optical pathways are illustrated schematically. Angles and dimensions are not to scale.

What claimed is:

1. An optical system for microarray laser scanning, comprising:
    a) an aperture-containing reflecting mirror comprising an aperture and a reflecting surface, wherein the aperture on the aperture-containing reflecting mirror allows an excitation light to pass through, and wherein the reflecting surface of the aperture-containing reflecting mirror allows emission light from a microarray to be reflected;
    b) a light forwarding system for generating the excitation light, wherein the light forwarding system comprises a first laser generator, a second laser generator, a beam splitter, and a light chopper, wherein the beam splitter transmits light generated by the first laser generator and reflects light generated by the second laser generator, and wherein the light chopper allows light generated by one laser generator to go through while blocking light generated by another laser generator at each time, and
    c) a first reflecting mirror optically positioned between the first laser generator and the beam splitter and a second reflecting mirror optically positioned between the beam splitter and the aperture-containing reflecting mirror, wherein light generated by the first laser generator is first reflected by the first reflecting mirror before it is transmitted by the beam splitter, and wherein light coming from the beam splitter is first reflected by the second reflecting mirror before it passes through the aperture of the aperture-containing reflecting mirror.

2. The optical system of claim 1, wherein the shape of the aperture-containing reflecting mirror is selected from the group consisting of circle, oval, regular shape, and irregular shape.

3. The optical system of claim 1, wherein the shape of the aperture of the aperture-containing reflecting mirror is selected from the group consisting of circle, oval, regular shape, and irregular shape.

4. The optical system of claim 1, further comprising an excitation objective lens for focusing the excitation light passing through the aperture-containing reflecting mirror.

5. An optical system for microarray laser scanning, comprising:
    a) an aperture-containing reflecting mirror comprising an aperture and a reflecting surface, wherein the aperture on the aperture-containing reflecting mirror allows an excitation light to pass through, and wherein the reflecting surface of the aperture-containing reflecting mirror allows emission light from a microarray to be reflected;
    b) a light forwarding system for generating the excitation light, wherein the light forwarding system comprises a first laser generator, a second laser generator, a beam splitter, and a light chopper, wherein the beam splitter transmits light generated by the first laser generator and reflects light generated by the second laser generator, and wherein the light chopper allows light generated by one laser generator to go through while blocking light generated by another laser generator at each time, wherein the light forwarding system further comprises matching light filter optically positioned in front of at least one of the two laser generators; and
    c) an excitation objective lens for focusing the excitation light passing through the aperture-containing reflecting mirror.

6. The optical system of claim 5, wherein the shape of the aperture-containing reflecting mirror is selected from the group consisting of circle, oval, regular shape, and irregular shape.

7. The optical system of claim 5, wherein the shape of the aperture of the aperture-containing reflecting mirror is selected from the group consisting of circle, oval, regular shape, and irregular shape.

8. An optical system for microarray laser scanning, comprising: a) an aperture-containing reflecting mirror comprising an aperture and a reflecting surface, wherein the aperture on the aperture-containing reflecting mirror allows an excitation light to pass through, and wherein the reflecting surface of the aperture-containing reflecting mirror allows emission light from a microarray to be reflected;
  b) a light forwarding system for generating the excitation light, wherein the light forwarding system comprises a first laser generator, a second laser generator, a beam splitter, and a light chopper, wherein the beam splitter transmits light generated by the first laser generator and reflects light generated by the second laser generator, and wherein the light chopper allows light generated by one laser generator to go through while blocking light generated by another laser generator at each time, wherein the light forwarding system further comprises an attenuator optically positioned behind the beam splitter, wherein light coming from the beam splitter is adjusted by the attenuator; and
  c) an excitation objective lens for focusing the excitation light passing through the aperture-containing reflecting mirror.

9. The optical system of claim 8, wherein the shape of the aperture-containing reflecting mirror is selected from the group consisting of circle, oval, regular shape, and irregular shape.

10. The optical system of claim 8, wherein the shape of the aperture of the aperture-containing reflecting mirror is selected from the group consisting of circle, oval, regular shape, and irregular shape.

11. An optical system for microarray laser scanning, comprising:
  a) an aperture-containing reflecting mirror comprising an aperture and a reflecting surface, wherein the aperture on the aperture-containing reflecting mirror allows an excitation light to pass through, and wherein the reflecting surface of the aperture-containing reflecting mirror allows emission light from a microarray to be reflected;
  b) a light forwarding system for generating the excitation light, wherein the light forwarding system comprises a first laser generator, a second laser generator, a beam splitter, and a light chopper, wherein the beam splitter transmits light generated by the first laser generator and reflects light generated by the second laser generator, and wherein the light chopper allows light generated by one laser generator to go through while blocking light generated by another laser generator at each time; and
  c) a light collection system for collecting the emission light, wherein the light collection system comprises a detector and an emission objective lens optically positioned between the detector and the aperture-containing reflecting mirror, wherein the light collection system further comprises a pinhole optically positioned between the emission objective lens and the detector and an emission light filter optically positioned between the aperture-containing reflecting mirror and the emission objective lens, wherein the emission light filter comprises two or more light filters for filtering light of different wavelengths.

12. An optical system for microarray laser scanning, comprising:
  a) an aperture-containing reflecting mirror comprising an aperture and a reflecting surface, wherein the aperture on the aperture-containing reflecting mirror allows an excitation light to pass through, and wherein the reflecting surface of the aperture-containing reflecting mirror allows emission light from a microarray to be reflected;
  b) an excitation objective lens for focusing the excitation light passing through the aperture-containing reflecting mirror;
  c) a light forwarding system comprising a first laser generator; a first reflecting mirror that reflects light generated by the first laser generator, a second laser generator; a beam splitter that transmits light reflected by the first reflecting mirror and reflects light generated by the second laser generator; a light chopper that allows light generated by one laser generator to go through while blocking light generated by another laser generator at a given time; and a second reflecting mirror that reflects the light allowed to go through, wherein light reflected by the second reflecting mirror passes through the aperture of the aperture-containing reflecting mirror; and a light collection system comprising an emission filter optically positioned behind the aperture-containing reflecting mirror, an emission objective lens optically positioned behind the emission filter, a pinhole optically positioned behind the emission objective lens, and a detector, wherein emission light reflected by the aperture-containing reflecting mirror passes the emission filter, emission objective lens, and pinhole sequentially before it reaches the detector; and
  d) matching light filter optically positioned in front of at least one of the two laser generators.

13. An optical system for microarray laser scanning, comprising:
  a) an aperture-containing reflecting mirror comprising an aperture and a reflecting surface, wherein the aperture on the aperture-containing reflecting mirror allows an excitation light to pass through, and wherein the reflecting surface of the aperture-containing reflecting mirror allows emission light from a microarray to be reflected;
  b) an excitation objective lens for focusing the excitation light passing through the aperture-containing reflecting mirror;
  c) a light forwarding system comprising a first laser generator; a first reflecting mirror that reflects light generated by the first laser generator, a second laser generator; a beam splitter that transmits light reflected by the first reflecting mirror and reflects light generated by the second laser generator; a light chopper that allows light generated by one laser generator to go through while blocking light generated by another laser generator at a given time; and a second reflecting mirror that reflects the light allowed to go through, wherein light reflected by the second reflecting mirror passes through the aperture of the aperture-containing reflecting mirror; and a light collection system comprising an emission filter optically positioned behind the aperture-containing reflecting mirror, an emission objective lens optically positioned behind the emission filter, a pinhole optically positioned behind the emission objective lens, and a detector, wherein emission light reflected by the aperture-containing reflecting mirror passes the emission filter, emission objective lens, and pinhole sequentially before it reaches the detector; and
  d) an attenuator optically positioned between the beam splitter and the second reflecting mirror.

* * * * *